United States Patent [19]

O'Neill et al.

[11] Patent Number: 4,604,365
[45] Date of Patent: Aug. 5, 1986

[54] IMMUNOPRECIPITATION ASSAY

[75] Inventors: Sean P. O'Neill, Bethesda; Joseph Wu, Gaithersburg, both of Md.

[73] Assignee: Electro-Nucleonics, Inc., Fairfield, N.J.

[21] Appl. No.: 406,762

[22] PCT Filed: May 28, 1982

[86] PCT No.: PCT/US82/00737

§ 371 Date: Jul. 1, 1982

§ 102(e) Date: Jul. 1, 1982

[87] PCT Pub. No.: WO82/04323

PCT Pub. Date: Dec. 9, 1982

Related U.S. Application Data

[63] Continuation-in-part of Ser. No. 269,727, Jun. 2, 1981, abandoned.

[51] Int. Cl.$^4$ ............................................. G01N 33/53
[52] U.S. Cl. .................................... 436/528; 436/536; 436/805; 436/808; 436/815; 436/823
[58] Field of Search ............... 436/528, 536, 805, 808, 436/815, 823

[56] References Cited

U.S. PATENT DOCUMENTS

| | | |
|---|---|---|
| Re. 29,169 | 4/1977 | Schuurs . |
| 3,489,522 | 1/1970 | McConnell . |
| 3,654,090 | 4/1972 | Schuurs . |
| 3,690,834 | 9/1972 | Goldstein . |
| 3,791,932 | 2/1974 | Schuurs . |
| 3,817,837 | 6/1974 | Rubenstein . |
| 3,839,153 | 10/1974 | Schuurs . |
| 3,850,752 | 11/1974 | Schuurs . |
| 3,875,011 | 4/1975 | Rubenstein . |
| 3,879,262 | 4/1975 | Schuurs . |
| 3,935,074 | 1/1976 | Rubenstein . |
| 3,976,763 | 8/1976 | Spector . |
| 4,016,043 | 4/1977 | Schuurs . |
| 4,038,143 | 7/1977 | Juni . |
| 4,066,744 | 1/1978 | Price . |
| 4,150,949 | 4/1979 | Smith . |
| 4,152,411 | 5/1979 | Schall . |
| 4,230,683 | 10/1980 | Decker . |
| 4,401,765 | 8/1983 | Craig ................................. 436/533 |

OTHER PUBLICATIONS

Wu, J. W. et al., Clinical Chemistry, 27(6), Abstract 341, 1092 (1981).
Dugan, S. et al., Clinical Chemistry, 28(5), 1190-1191 (1982).
Wu, J. W. et al., Clinical Chemistry, 28(4), 659-661 (1982).
I. Deverill et al., J. Immunol. Methods, 38, 191-204 (1980).
T. Nishikawa et al., Clinica Chimica Acta, 91, 59-65 (1979).
T. Nishikawa et al., J. Immunol. Methods, 29, 85-89 (1979).
P. R. Finley et al., Clin. Chem., 27(3), 405-409 (1981).
"Automated Immunoanalysis", Part 1, R. F. Ritchie, ed., Chapter 15 by J. Gauldie et al., Marcel Dekker, New York, 1978.

Primary Examiner—Sidney Marantz
Attorney, Agent, or Firm—Wyatt, Gerber Shoup, Scobey and Badie

[57] ABSTRACT

Competitive assay procedure for determining the concentration of physiologically active haptens in which the hapten is bound to an immunogenic carrier and competes for binding sites on antibodies against the hapten. Actual concentration is determined by comparison with standard curves.

12 Claims, 5 Drawing Figures

IMMUNOPRECIPITATION ASSAY

RELATED APPLICATION

This application is a continuation-in-part application of co-pending application Ser. No. 269,727 filed June 2, 1981 now abandoned.

BACKGROUND OF THE INVENTION

Therapeutic monitoring of various agents present in serum and other body fluids is a rapidly growing segment of the clinical laboratory testing field. With therapeutically effective agents, the purpose of the monitoring is to indicate adjustments in dosage so as to maintain a patient at a therapeutically effective drug level. Below this level, the agent may be toxic. Such monitoring is, as will be recognized, important not only for following changes in levels of useful therapeutic agents, but also for ascertaining levels of a wide variety of physiologically active substances which may be present in body fluids including, for example, vitamins, enzymes and hormones.

Methods available for the fast and accurate quantitative or qualitative determination of biologically active substances, at low concentrations are limited in number. The physicians diagnosis of the patient or confirmation of the diagnosis frequently involves the detection and/or quantitation of one or more substances in body fluids. The ability to detect rapidly in body fluids the presence and amounts of such materials is often critical to the patient's life.

Several methods have, in the past, been used for the assay of body fluids, notably radioimmunoassay, thin layer chromatography, enzyme immunoassay and fluorescence immunoassay systems. The use of a radioimmunoassay technique suffers from several disadvantages among which are the hazards associated with or inherent in radioactive materials, associated handling problems, instability, the need for expensive equipment for the assays and the difficulties associated with the manipulation and separation of the free and bound forms of the raidoactive materials. Thin layer chromatography is often quite slow in the development of the chromatogram, is sensitive to the presence of a variety of interfering factors and suffers from the lack of reporducibility or reliability. The use of enzyme or fluorescence immunoassay requires dealing with, and knowledge of very complicated chemistry involved in their preparation, storage and usage of the required reagents. Also, the method is sensitive to variations in environmental conditions, so that the methods have not proven entirely satisfactory to the users. Nephelometry has also been employed but the incubation times required have limited the practicality of the procedure, especially for automation. Additionally, the procedure requires the use of special equipment which is not routinely avaliable in commercial laboratories. Additionally, unless the laser nephelometer is employed interference noise or background effects are so bothersome that the technique cannot be applied directly to serum. Additionally, they cannot be used at low wavelengths where one would obtain best sensitivity because of the unavoidable increase in output power which renders them dangerous. (Deverill and Reiner, Journal of Immunological Methods 38 (1980) 191-204, at page 195).

The Invention

A procedure has now been discovered which substantially alleviates the problems aforesaid and makes possible the detection and accurate determination of small amounts of therapeutic drugs and other low molecular weight haptens in various body fluids and other samples. In accordance with the procedure, a competitive assay is set up for available antibody sites between the hapten, the concentration of which is to be determined and the same hapten conjugated to a carrier.

The process of the invention will be principally employed for the determination of hapten concentrations in mammalian serum. It is, however, applicable to the determination of hapten concentrations in a variety of liquid samples including, for example, human serum and plasma, urine, spinal fluid, amnionic fluid, etc.

The immunoprecipitation assay procedure of the invention may be applied to low molecular weight physiologically active substances, which for convenience are termed "haptens" in this description and claims. Haptens have been generally defined as protein-free substances with chemical configurations such that they can react with specific antibodies but not such that they are capable of causing the formation of antibodies. For the purposes of this description, they include a wide variety of physiologically active materials, for example, antibiotics such as tetracycline, chloromycetin, streptomycin and aminoglycoside antibiotics such as amikacin, erythromycin, gentamicin, kanamycin, netilimicin, sisomicin, tobramycin and vancomycin; anti-eptileptic drugs such as carbamazepine, Dilantin (phenytoin), ethosuximide, phenobarbitol, desipramine and imipramine; anti-arrythmics such as digoxin, digitoxin, propanolol, procainamide and disopyramide; alkaloids such as methadone, caffeine, dextromoramide, dipipanone, phenodoxone and darvone, catecholamines such as ephedrine, epinephrine and benzidine; abused drugs such as barbituates, benzodiazepines, chlordiazepoxide, diazepam, oxazepam and marijuana; amino acids; steroids including estrogens, gestogens and androgens; vitamins; and sugars. Monitoring of the metabolites of these various compounds is also of interest.

For convenience, the compounds to which this invention is applicable will hereinafter be generically referred to as haptens or drugs. As the description of the invention proceeds, reference will be made to hapten-carrier conjugates or drug-carrier conjugates, and to the reaction products of the conjugates with antibodies.

Desirable therapeutic ranges for a number of haptens have been determined. Some of them are listed in Table I which should not be regarded as limiting with respect to the haptens to which this invention is applicable.

TABLE I

| Function | Drugs | Therapeutic Concentration Range | |
|---|---|---|---|
| Antibiotic | Gentamicin | 2-12 | µg/ml |
| | Tobramycin | 2-10 | µg/ml |
| | Amikacin | 5-40 | µg/ml |
| | Kanamicin | 5-40 | µg/ml |
| | Chloroamphenicol | 2-10 | µg/ml |
| Anti-epileptics | Phenobarbitol | 10-40 | µg/ml |
| | Theophylline | 10-20 | µg/ml |
| | Dilantin | 10-20 | µg/ml |
| | Primidone | 8-12 | µg/ml |
| | Ethosuximide | 40-80 | µg/ml |
| | Carbamazepine | 5-10 | µg/ml |
| | Valproate | 50-100 | µg/ml |
| Anti-depressives | Nortriptyline | 50-150 | µg/ml |

TABLE I-continued

| Function | Drugs | Therapeutic Concentration Range | |
|---|---|---|---|
| Anti-arrythmic | Desipramine | 150–250 | μg/ml |
| | Imipramine | 100–200 | μg/ml |
| | Digoxin | 0.5–2.0 | μg/ml |
| | Digitoxin | 10–30 | μg/ml |
| | Propanolol | 50–100 | μg/ml |
| | Procainamide | 3–10 | μg/ml |
| | Disopyramide | 2–4 | μg/ml |

The specific compounds listed above and others, as is well known, all have desirable concentration ranges in which they exert their optimum therapeutic effects. Other physiologically active haptens from the above exemplary list do not have any desirable concentration. They are, in fact, toxic. However, it is often of critical importance for the physician to know the concentration of these materials in plasma or other body fluid so that appropriate life saving measures or detoxifications steps can be taken. Still others are not therapeutic in the sense that antibiotics are therapeutic, but may desirably be at a certain level in body fluids to maintain the health and continued well being of the subject. The concentration of certain other materials may be of interest to test for certain metabolic diseases or for pregnancy.

In general, as in the list given in Table I, the concentration ranges are very low and vary over extremely wide ranges. Desirable concentrations differ by orders of magnitude, for example, from micrograms per millimeter to nanograms per milliliter.

For convenience, all concentration ranges to which the process of this invention applies, whether they be therapeutic ranges, toxic ranges, ranges which will help to maintain good health, test ranges or other ranges will be referred to herein as "concentration of ranges of interest".

The method of assay of this invention is based on competitive immunological reactions in which the reactants and all but one of the products are soluble in the test medium. Specifically the hapten, the hapten-carrier conjugate, the antibody and the hapten-antibody reaction product are soluble in the test medium, and the conjugate-antibody is not. Therefore, as more and more of the last mentioned reaction product forms, the turbidity of the test medium increases. To the extent that the hapten reacts with antibody, the turbidity will decrease.

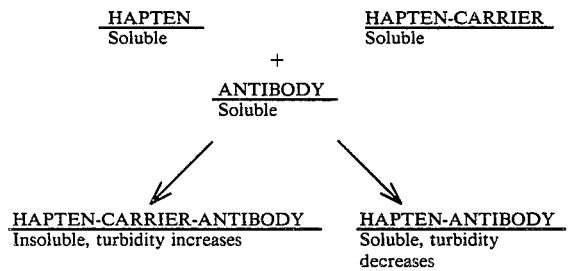

In the competitive assay, the soluble hapten present in the patient's serum or other body fluid competes with the soluble hapten-carrier (conjugate) for a limited number of available antibody sites thereby reducing the amount of insoluble conjugate-antibody complex which will form and concurrently decreasing the turbidity of the solution. The degree of turbidity, therefore, is inversely proportional to the concentration of free hapten in a test medium containing free hapten together with hapten-carrier, antibody, conjugate-antibody and hapten-antibody.

The first necessity for conducting the competitive assays of this invention is the preparation of a series of hapten-carrier conjugates of different hapten or drug to immunogenic carrier ratio.

As used herein, the term "immunogenic carrier" is meant to include those materials which have the property of independently eliciting an immunogenic response in a host animal when injected therein, and can be directly or indirectly coupled by covalent bonding to the hapten. Suitable materials include naturally occurring proteins, natural and synthetic polymeric compounds such as polypeptides, polysaccharides, polystyrene, polyacrylates and the like. Normally, for use in this invention, the molecular weight of the carrier will be at least 60,000 daltons.

For the preparation of the conjugate, there may be functional groups already present on the hapten and on the carrier. These may react directly to form conjugates. These groups include, for example, hydroxyl, amino and carboxyl groups. If no suitable functional group is present, it may be put in place. For example, with certain steroid haptens it may be possible to substitute an hydroxyl group on the molecule by fermentation procedures, or to monoesterify a hydroxyl group with a dicarboxylic acid to leave a free carboxyl group.

Other reagents may be employed to effect coupling between hapten and carrier. These include, for example, dialdehydes such as glutaric aldehyde; hydrazines; dinitrodiphenylsulfone, diisocyanates such as tolueneiisocyanate; di- or tri-chlorotriazines; carbodiimides; cyanogen bromide and diazo compounds.

Procedures for forming conjugates by any of the methods suggested above will be familiar to those skilled in the art.

Since the carrier compound will normally carry a large number of functional groups, it is apparent that, within reason, any selected number of hapten molecules can be joined to a particular carrier. Thus, the hapten-carrier ratio may vary from as low as 1:1 to as high as 100:1 or even higher. An important aspect of this invention is the discovery that when decreasing optical density at wave lengths from 280–600 nm is plotted as the ordinate against increasing concentration of free hapten in media containing conjugate, free hapten, hapten-conjugate, antibody and hapten-antibody, the shape of the curve will vary with changing drug:carrier ratios at which the concentration of free hapten can be obtained with optimum sensitivity.

It will be apparent from the above that the number of hapten molecules attached to each molecule of carrier has an important effect on the use of turbidity measurements as a method of immunoassay. At low ratios of hapten to carrier, e.g. 3:1, the conjugate will not produce sufficient turbidity to be of practical use as a measuring tool. At the other extreme of high hapten to carrier ratio, e.g. 50:1, the hapten-conjugate-antibody reaction will produce too much turbidity to allow sensitive measurements of changes in turbidity.

Sensitivity to changes in free hapten concentration will be very poor at both ends of the scale.

This invention will be better understood by reference to the figures in which.

Figure 1:
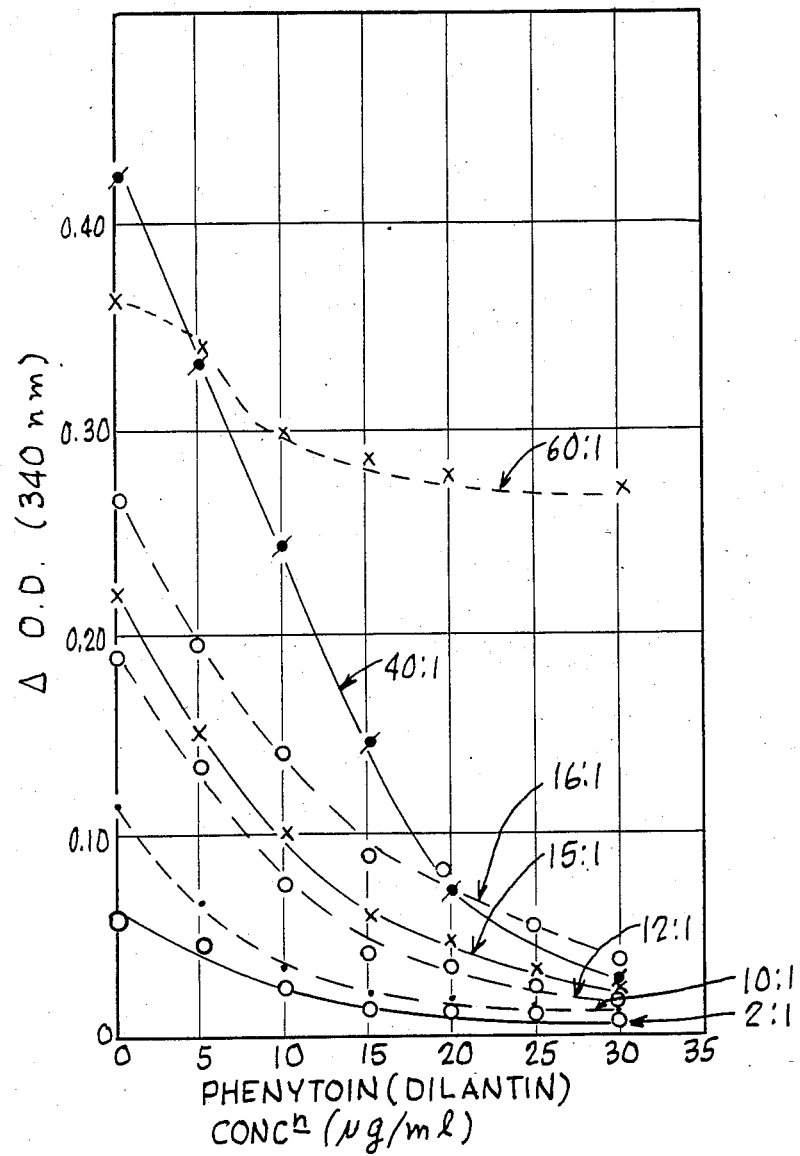
FIG. 1 is a graph of standard curves in which optical density of separate mixtures containing fixed amounts of conjugate and soluble antibody to the conjugate is plotted against increasing hapten concentration, the conjugate being Dilantin-human serum albumin (HSA).

Referring to Table I, it will be seen that the concentration range of interest for Dilantin is 10-20 $\mu$g/ml. Referring to FIG. 1, it will be seen that over the hapten concentration range of from 10-20 $\mu$g/ml, the optical density change is relatively small when the hapten to carrier ratio is low, e.g. 6:1 or 10:, and that the same is true at a high ratio, e.g. 60:1. However, if the hapten to carrier ratio is from 12:1 to 40:1, there is a relatively large change in optical density with relatively small changes in hapten concentration. This is the region of optimum sensitivity. It is the region in which the average slope of the curve is such that there is sufficient decrease in optical density with increase in hapten concentrations so that there is optimum response in optical density change to change in concentration. As shown in FIG. 1, the average slopes of the curves in the Dilantin concentration range from 10 to 20 $\mu$g/ml at Dilantin-HSA ratios from 12:1 to 40:1 is from about 30° to 60°. It will be known, however, that if the scale of the graph is changed, the average slope will also change so that it is difficult to assign specific values to the average slope of optimum sensitivity. It will be apparent, however, that no matter what scale is selected, the graph will show a range of Dilantin-HSA ratios where there is optimum sensitivity and this will be readily recognized by the shape of the curve.

Still another explanation of optimum sensitivity is based on the recognition that sensitivity is at a minimum at both high and low hapten-carrier ratios and passes through a maximum, so that a curve plotting sensitivity against hapten-carrier ratio may start at a low point at the lowest hapten-carrier ratio pass, through a maximum as the hapten carrier ratio incrases, and then return to the low value with increasing hapten-carrier ratio. The basis of this invention is the discovery that for the hapten, the concentration of which is to be determined, there is a range of hapten-carrier ratios where optimum sensitivity is achieved in the concentration range of interest.

Maximum sensitivity is, of course, the ability to recognize minimum changes in hapten concentration. As a practical matter, it is not essential to obtain maximum sensitivity to achieve useful measurements. The sensitivity should, however, be as close to maximum as is reasonably possible. More specifically, it should be what is characterized herein as "optimum sensitivity". To quantize the sensitivity, it is reasonable to say that there is optimum sensitivity when there is an ability to recognize concentration changes of ±5%.

Figure 2:
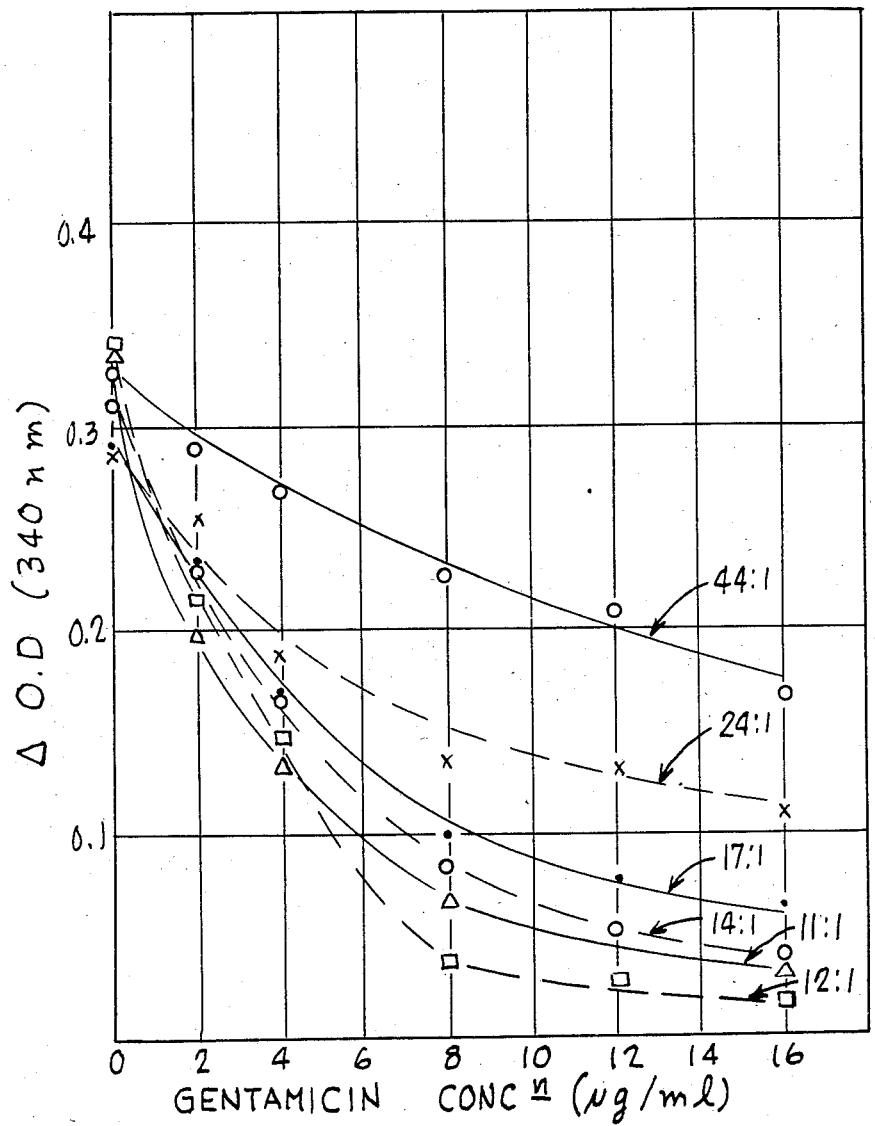
FIG. 2 is similar to FIG. 1 except that the conjugate is gentamicin-HSA.

FIG. 2 is similar to FIG. 1 except that the drug under investigation is the antibiotic gentamicin. The therapeutic drug range is 2 to 12 $\mu$g/ml. It will be seen that at low drug:carrier ratios, e.g. 11:1, 12:1 or 14:1, there is relatively little change in optical density over the range of 8 to 16 $\mu$g/ml. An acceptable assay system must provide the possibility of optimum sensitivity in this range since it overlaps the therapeutic range. At high drug:carrier ratio e.g. 44:1, discrimination or sensitivity is not good along the entire length of the standard curve.

Intermediate ratios of 17:1 to 24:1 provide the opportunity for optimum sensitivity over all of the required assay range for this antibiotic.

Figure 3:
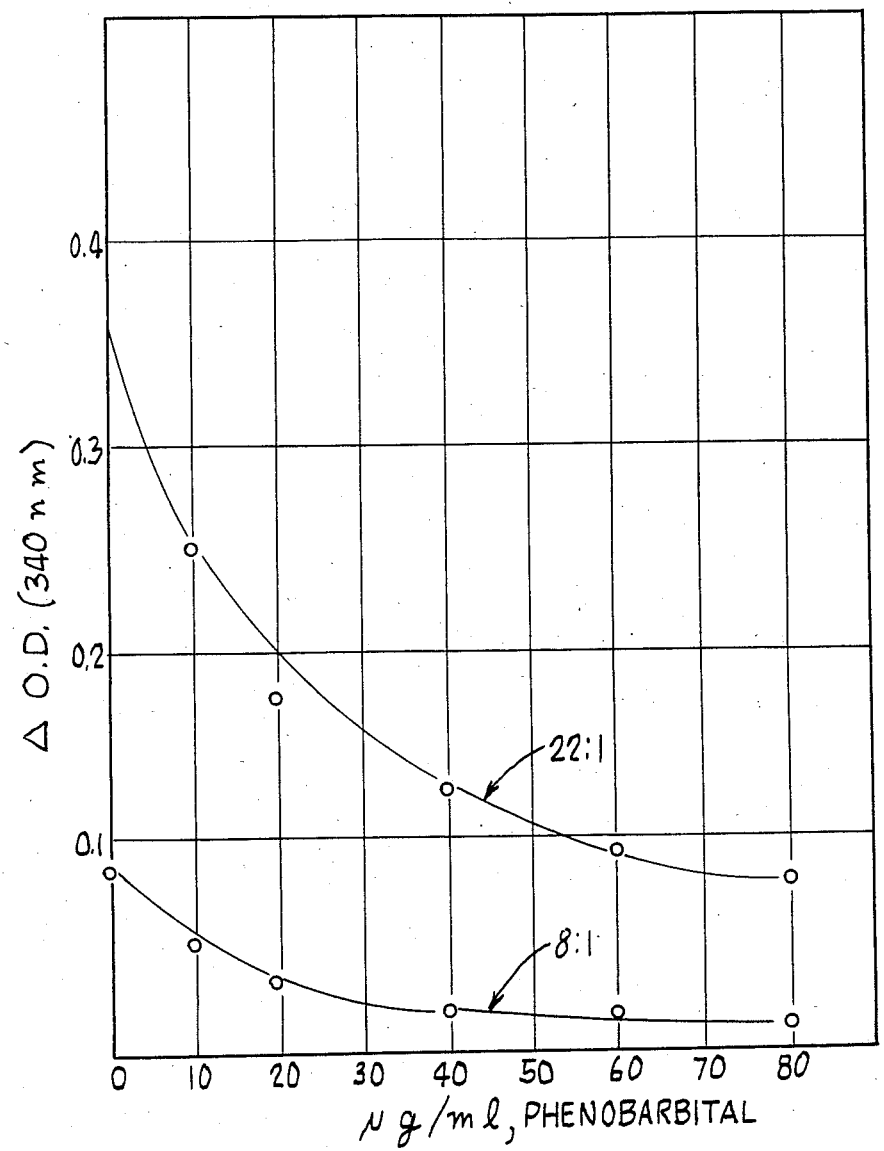
FIG. 3 is similar to FIG. 1 except with a smaller number of curves and the conjugate is phenobarbitol-HSA.

FIG. 3 shows only two curves. Curve A is phenobarbitol-HSA ratio of 8:1. Curve B is at a ratio of 22:1. It will be seen that at a ratio of 8:1 the change in optical density at the concentration range of interest (10-40 $\mu$g/ml) is very low, but at a ratio of 22:1 the change is very marked. It is, in fact, sufficiently great so that phenobarbitol concentrations can be obtained as described herein. In fact, ratios of from 15:1 to 30:1 will permit the determination of optimum sensitivity.

Figure 4:
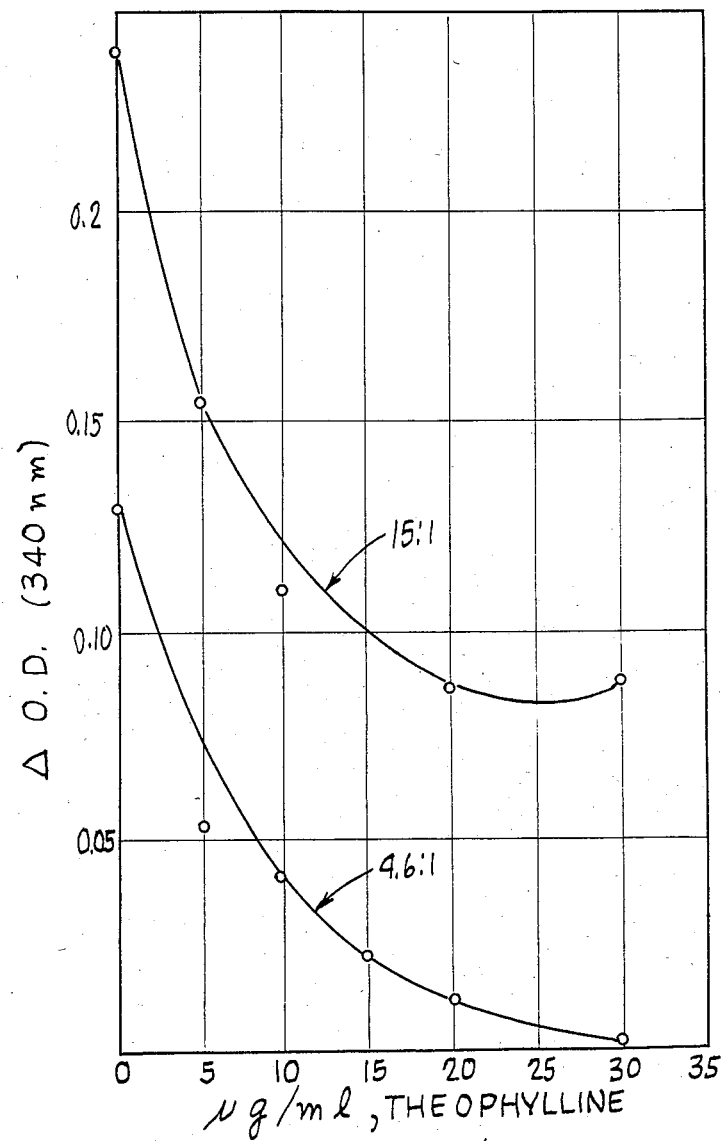
FIG. 4 is similar to FIG. 1 except with a smaller number of curves and the conjugate is theophylline-HSA.

FIG. 4 is similar to FIG. 3. Curve D shows that with theophylline a hapten:carrier ratio of 4.6:1 will not permit determination of optimum sensitivity at the range of interest because the optical density is too low. There is not sufficient turbidity. At a concentration of 10 $\mu$g/ml the optical density is only 0.04. At 20 $\mu$g/ml it is only 0.02. However, at a ratio of 15: not only is the optical density sufficiently high, but also the change in optical density over the concentration range of interest is sufficiently high to permit accurate measurements. For theophylline the useful hapten:carrier range is from about 10:1 to 20:1.

Figure 5:
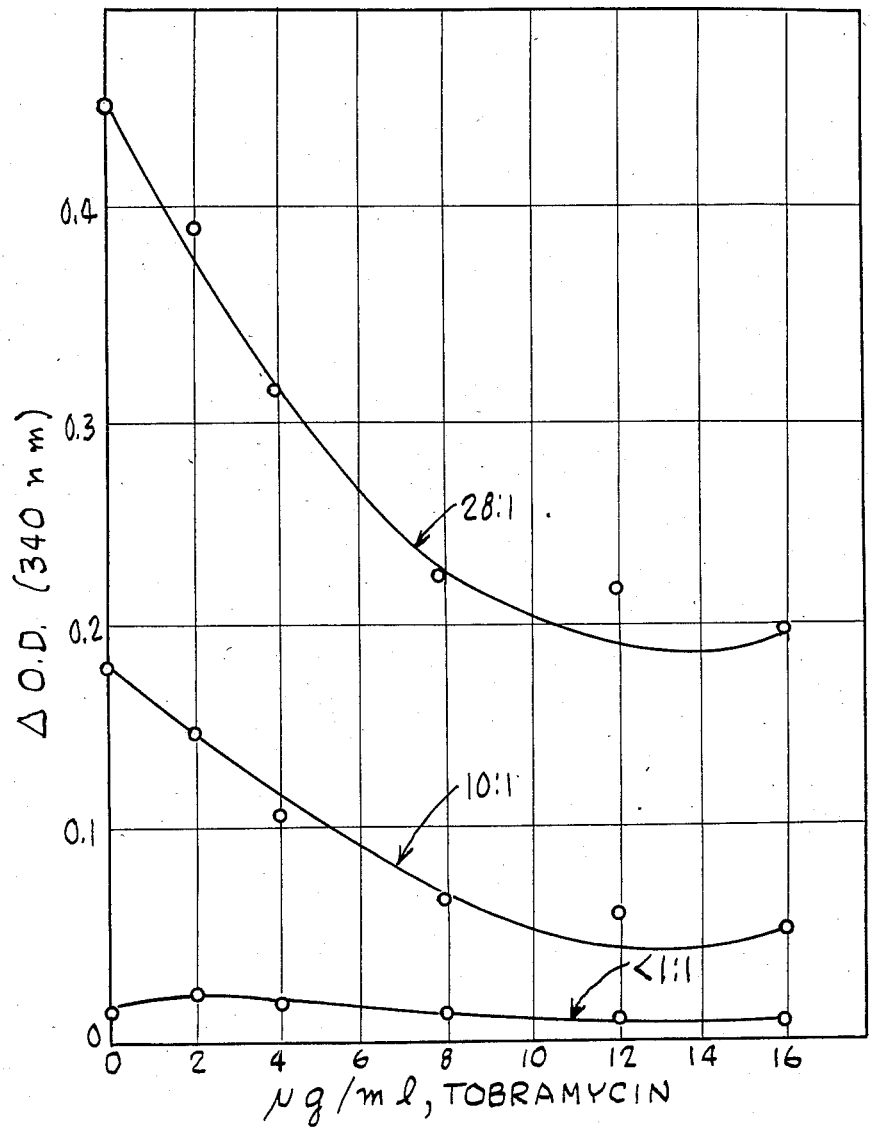
FIG. 5 is similar to FIG. 1 except with a smaller number of curves and the conjugate is tobramycin-HSA.

FIG. 5 shows that with tobramycin-HSA at ratios of under 1:1 and 10:1 the optical densities are too low for useful measurements and the changes in optical densities are not sufficient in the concentration range of interest, i.e. 2 to 10 $\mu$g/ml. However, at 28:1 the optical density and change in optical density is acceptable. It was found that tobramycin-HSA ratios of 30:1 were not attainable. The useful ratios for this antibiotic are from 20:1 to 28:1.

It sometimes happens that at high ratios the hapten-carrier conjugate is insoluble. Clearly such conjugates are not useful for the practice of this invention.

As stated above, the preparation of the conjugate in which the hapten is covalently bound to the immunogenic carrier is in accordance with techniques well known to those skilled in the art. The drug:carrier ratio will normally depend upon the amount of drug or hapten employed. For high ratios of drug to carrier, normally high concentrations of drugs will be employed. The course of the reaction and the determination of the drug:carrier ratio of the final product can be determined by any of a number of methods, for example, ultraviolet spectrophotmetry, radiolabeling and the like. Suitable illustrations of the synthesis of conjugates with various ratios are given in the examples.

Antisera containing the antibody to the hapten-carrier conjugate may be raised in any convenient mammal, for example, goat, sheep, horse or rabbit or by other standard procedures including the hybridoma technique. The hapten-carrier ratio in the conjugate used to raise the antibody is not critical. Any of the conjugates synthesized for the preparation of the standard curves may be employed. The conjugate mixed with an adjuvant, for example, Freund's adjuvant is injected into the selected animal and the animal is bled in about one month. The serum containing the antibody is separated from the whole blood.

It is preferred, but not essential, that the carrier used in the conjugate for the preparation of the antisera be different from the carrier employed in the conjugate used in the preparation of standard curves. The use of different carriers limits the possibility of cross reactions. For example, HSA can be used in the conjugates for the standard curves, and bovine serum albumin (BSA) can be used to prepare antisera.

A particular advantage of the procedure of this invention is that by selecting the correct drug:carrier ratio it is possible to determine the optical density in the ultraviolet region of the spectrum at a wavelength of from 280-600 nm. At these wavelengths, there is improved sensitivity compared to the sensitivity which can be attained at higher wavelengths, the techniques are generally less difficult and the available instruments, such as the spectrophotometer, Centrifugal Analyzer, and Clinical Chemistry Analyzer are relatively inexpensive, easy to use and readily adaptable to automation. The procedures are sufficiently rapid so that they are readily adaptable to automation techniques.

To achieve optimum sensitivity measurements, it is best to use concentrations of antisera and conjugate which give maximum absorbance at the selected wavelength. These concentrations are readily determined by standard measurements. To make the determinations, antisera raised by the conjugate is adjusted by serial dilution to values of, say 1:1, 1:10, 1:20-1:160, and samples of such dilution are allowed to react with similarly diluted conjugate. The optical density is determined for each reaction at a selected wavelength from 280 to 600 nm. The wavelength will be the same wavelength as is used when preparing the standard curves. These measurements are made for a series of high to low drug:carrier ratios. There will be an optimum absorbance for each drug:carrier ratio and each antisera dilution. For instance, the optimum absorbance for gentamicin-HSA conjugate with a 1:50 dilution of antisera is 1:10.

The reactions are carried out in aqueous media which ideally, but not necessarily, will be the same media employed to prepare the standard curves and to determine the concentration of the hapten in a sample. The medium may contain about 2 to 5% polyethylene glycol (molecular weight 40,000 to 80,000, preferably about 60,000) as an accelerator and in some instances, up to about 10% of a water miscible polar organic solvent to aid solubility. These include alcohols, ketones and amides, for example, methyl or ethyl alcohol, acetone and dimethylformamide.

The pH of the medium will normally be from about 3 to 11, preferably 6 to 9. Various buffers together with sufficient dissolved salt to be isotonic may be employed. Illustrative buffers include carbonate, phosphate, borate, Tris, barbital and the like. The buffer employed is not critical to the present invention, but in particular measurements, one buffer may be preferred over another.

Moderate temperatures are normally employed for carrying out the measurements and usually constant temperatures during the period of assay is employed. The temperatures typically range from about 20° C. to 45° C., more usually from about 25° C. to 40° C.

Once the conditions for maximum absorbance have been determined, it is possible to set up the competitive immunoassay by mixing the sample to be determined with the selected dilution of antisera and conjugate. The first assay is with known concentrations of hapten sample in human plasma or other body fluid. The competitive immunoassay is followed by plotting optical density against hapten concentration. From these standard curves, it is possible to select a conjugate with a drug:carrier ratio which will provide optimum sensitivity in the concentration range of interest. Once the standard curves have been prepared and the best drug:carrier ratio determined, it is possible to conduct competitive assays using samples with unknown concentrations of hapten. Typically, these samples will be human serum containing unknown concentrations of drugs. The optical density of the mixture containing the conjugate at the optimum dilution, the antisera at the optimum dilution and the unknown concentration of hapten will be compared with the standard curves to identify the concentration of hapten in the serum sample.

In summary, the process of this invention comprises as applied to the determination of haptens in blood, the steps of:

1. Preparing a series of drug:carrier conjugates at different drug-carrier ratios. These will be prepared in aqueous media amd will normally contain from 2-10 mg protein/ml.

2. Preparation of antibody, for example, by use of a conjugate to raise antisera in a mammal.

3. Collect the antisera and separate the serum.

4. Determine the conditions for maximum absorbance at a selected wavelength for each antisera and each conjugate by comparison of optical densities.

5. Prepare standard curves by plotting the change in optical density against the change in hapten concentration for a variety of conjugates with different drugs:carrier ratios to select the drug:carrier ratio which gives optimum sensitivity over the hapten range of interest.

6. Determining the concentration of hapten in an unknown sample by mixing the sample with antisera and the selected drug:carrier conjugates and determining the optical density.

7. Compare the optical density thus obtained with the optical density of known samples as shown by the standard curves to determine the concentration of hapten in the sample measured.

With samples other than blood serum, there will be appropriate modifications in the process outlined above.

Test kits may be made available for the convenient practice of this invention. The kits will contain the ingredients to prepare standard curves and may contain sufficient buffered liquid to utilize as the reaction solvent. The kits, therefore, will contain hapten at various standard concentrations, antisera to the hapten, and conjugate dissolved in the test media solvent. The drug:carrier ratio in the conjugate will be at a selected value to provide optimum sensitivity, and the antisera and conjugate solutions will be at proper dilutions to provide optimum absorbance as described above. Clinical laboratories which in the course of a day will conduct a large number of determinations for the same hapten will not need to prepare standard curves for each determination. A test kit for such laboratories may omit the samples of hapten at standard concentrations, provided that at least one set of such samples is available.

A specific advantage of the process of this invention is the high in day and between day precision of the assays. The concentration values for aliquots of the same sample measured on the same day or on successive days are measurable with a degree of precision which is consistent with good medical practice.

The following non-limiting examples are given by way of illustration only.

EXAMPLE I

Determination of Gentamicin in Serum

I. The formation of a gentamicin-human serum albumin conjugate is achieved as follows:

A. To a solution of 100 mg of human serum albumin in 10 ml 0.01 M phosphate buffer pH 7.4 containing 0.15 M NaCl, 150 mg of gentamicin sulfate in 8 ml of distilled water containing 2 ml 124-I-gentamicin as tracer (approximately 600 cpm/ml) are added with stirring. To the mixture is added portionwise with stirring 1 gm of 1-ethyl-3-(3-dimethyldaminopropyl) carbodiimide HCl over a period of 20 minutes. The resulting reaction mixture is stirred at room temperature for another 20 minutes and the excess condensing agent and small molecules are then removed by dialyzing against 0.01 M phosphate buffer containing 0.15 M MaCl pH 7.4 at 4° C. The ratio of the resulting conjugate is determined from the 125-I-tracer to be 17 molecules of gentamicin per molecule of human serum albumin.

B. When the procedure A is repeated omitting the 125-I-gentamicin tracer, the conjugates are substantially identical in properties.

C. When the procedure A is repeated using the following quantities and reaction conditions, 100 mg human serum albumin; 325 mg gentamicin sulfate; 2 gm 1-ethyl-3-(3-dimethylaminopropyl) carbodiimide HCl; same amount of 125-I-gentamicin tracer; reaction time: One hour at room temperature and 24 hours at 4° C., the ratio of the resulting conjugate is 44 molecules of gentamicin per molecule of human serum albumin.

D. When the procedure A is repeated using the following quantities and reaction conditions, 100 mg human serum albumin; 200 mg gentamicin sulfate; 1.5 mg 1-ethyl-3(3-dimethylaminopropyl)carbodiimide HCl; same amount of 125-I-gentamicin tracer; reaction time, 30 minutes at room temperature, the ratio of the resulting conjugate is 24 molecules of gentamicin per molecule of human serum albumin.

II. Determination of the equivalent point of gentamicin per human serum albumin conjugate bound to gentamicin antibody.

A series of dilution of gentamicin conjugate (the ratio of gentamicin/albumin, 17) is titrated by an appropriate dilution of gentamicin antibody in an aqueous diluting agent which consists of 3% polyethyleneglycol (molecular weight 60,000), 0.25 M NaF and 0.15 M NaCl, pH 7.5, yielding a Gaussian type of curve. A typical titration result after 30 minutes incubation at room temperature is obtained at 340 n, from a spectrophotometer and tabulated in Table I.

Table I. Data obtained from the titration of a series of dilution of gentamicin-human serum albumin conjugate (0.01 ml) with a dilution of 1:50 gentamicin antibody.

| Gentamicin Conjugate Dilution | Absorbance |
|---|---|
| Undiluted (4 mg protein/ml) | 0.371 |
| 1:2 | 0.530 |
| 1:5 | 0.705 |
| 1:10 | 0.718 |
| 1:20 | 0.481 |
| 1:40 | 0.276 |
| 1:80 | 0.149 |
| 1:160 | 0.086 |

From the tritation, the dilution yielding the maximum absorbance (1:10) is used to establish the ratio of antiserum and gentamicin conjugate as the reagents for the construction of a standard curve.

III. Construction of a Gentamicin Standard Curve and Determination of Unknown Patient Samples.

Standard solutions are prepared from gentamicin dissolved in gentamicin free normal human serum at concentrations ranging from 2 to 16 µg/ml. The procedure for the assay is as follows: A disk containing 20 numbered wells is positioned on a supporter (disks and supporter are manufactured by Electro-Neucleonics, Inc.). Each well has two compartments: sample compartment and reagent compartment. A 10 µl of gentamicin conjugate (1:10 dilution) and a 50 µl of various standard solutions (or patient samples) are pipetted into each sample compartment. A 0.50 ml of gentamicin antibody (1:50 dilution) is pipetted into each reagent compartment. The disk is fitted into an instrument GEMENITM ™ (Electro-Neucleonics, Inc.) operated by a specific computer card, giving 4 minutes incubation at 37° C. and 3 minutes mixing and reaction. A standardization curve is constructed by subtracting the initial 6 second reaction absorbance reading from the 3 minute reaction absorbance reading for each sample. This plot of data is shown in in FIG. 2.

Assay of gentimicin in 11 patients' samples by the present assay and, for comparison, an enzyme immunoassay gives, excluding two severely lipemic samples from the serum patient, a regression equation, $$Y=0.87X+0.11$$

with the correlation coefficient, 0.973.

The precision of this assay is tested by assaying two control sera within-day assay and three control sera for between-day assay as shown in Table II.

TABLE II

| | Precision of Gentamicin Assay | | |
|---|---|---|---|
| | N | X µg/ml | SD | CV % |
| Within-day | | | | |
| Control 1 | 10 | 1.55 | 0.36 | 23.3 |
| Control 2 | 21 | 6.90 | 0.53 | 7.5 |
| Between-Day | | | | |
| Control 1 | 6 | 3.19 | 0.76 | 23.5 |
| Control 2 | 6 | 5.10 | 0.50 | 9.8 |
| Control 3 | 6 | 10.30 | 1.10 | 10.6 |

As expected, the precision is best for the control value in the mid-range of the standard curve, where the therapeutic concentration is monitoring, i.e. 4–8 µg/ml.

EXAMPLE II

Determination of Dilantin in Serum

I. The formation of a dilantin-human serum albumin is achieved as follows:

To a solution of 40 mg of dilantin valeric acid (valeric acid derivative of dilantin) in 6 ml of a 1:5 mixture of pyridine:water, 40 mg of 1-ethyl-3-(3-dimethylaminopropyl) carbodiimide HCl are added with stirring and followed with 100 mg human serum albumin in 4 ml distilled water. The solution is stirred at room temperature for 30 minutes and then 20 mg more of 1-ethyl-3-(3-dimethylaminopropyl) carbodiimide HCl are added. The resulting reaction mixture is stirred at room temperature for 1½ hour and then dialyzed against 0.01 M phosphate buffer containing 0.15 M NaCl, pH 7.4 at 4° C. The ratio of the resulting conjugate analyzed spectrophotometrically to be about 40.

II. Determination of the equivalent point of dilantin-human serum albumin conjugate bound to the dilantin antibody.

A series of dilution of dilantin conjugate (the ratio of dilantin/albumin 40) is titrated by an appropriate dilution of dilantin antibody in an aqueous diluting agent which consists of 3% polyethylene glycol (molecular weight, 60,000), 0.25 M NaF and 0.15 M NaCl, pH 7.6, yielding a Gaussian type of curve. A typical titration result after 30 minutes incubation at room temperature is obtained at 340 nm from a spectrophotometer and tabulated in Table III.

Table III. Data obtained from the titration of a series of dilutions of dilantin-human serum albumin conjugate (0.01 ml) with a dilution of 1:50 dilantin antibody (0.50 ml).

TABLE III

| Dilantin Conjugate Dilution | Absorbance |
|---|---|
| Undiluted Protein (7.7 mg/ml) | 0.148 |
| 1:2 | 0.182 |
| 1:5 | 0.304 |
| 1:10 | 0.532 |
| 1:20 | 0.637 |
| 1:40 | 0.401 |
| 1:80 | 0.255 |
| 1:160 | 0.182 |
| 1:320 | 0.145 |

From the titration, the dilution yielding the maximum absorbance (1:20) is used to establish the ratio of antiserum and dilantin conjugate as the reagents for the construction of a dilantin standard curve.

III. Construction of a Dilantin Standard Curve and Determination of Unknown Patient Samples.

Standard solutions are prepared from dilantin stock solution which is then mixed with dilantin-free normal human serum, giving the desired concentration in the range of 5 to 30 μg/ml. The dilantin stock solution is prepared by dissolving the desired amount of dilantin in a small amount of of ethyl alcohol and then diluted with distilled water to the mark of a volumetric flask. The procedure for the assay is as follows: A disk containing 20 numbered wells is positioned on a supporter (disks and supporter are manufactured by Electro-Nucleonics, Inc.). Each well has two compartments: Sample compartment and reagent compartment. A 10 μl of dilantin conjugate (1:20 dilution) and a 10 μl of various standard solutions (or patients' samples) are pipetted into each sample compartment. A 0.50 ml of dilantin antibody (1:50 dilution) is pipetted into each reagent compartment. The disk is fitted into an instrument such as a centrifugal analyzer (for example: Genemi (Electro-Nucleonics, Inc., Fairfield, NJ) operated by a specific computer card, giving 4 minutes incubation at 37° C. and 3 minutes mixing and reaction. A standardization curve is constructed by subtracting the initial 6 second reaction absorbance reading from the 3 minute reaction absorbance reading for each sample. This plot of data is shown in FIG. 1.

IV. Precision and Accuracy for Clinical Assay

Assay of dilantin in 45 patients' samples by the present assay and enzyme immunoassay gives a regression equation, $$Y = 1.12X + 0.24$$

with the correlation coefficient, 0.963.

The precision of this assay is tested by assaying two control sera for within-day assay and five control sera for between-day assay as shown in Table IV.

TABLE IV

| | Precision of Dilantin Assay | | | |
|---|---|---|---|---|
| | | X | SD | |
| | N | μg/ml | | CV % |
| Within-Day | | | | |
| Control 1 | 24 | 11.40 | 0.53 | 4.6 |
| Control 2 | 24 | 16.60 | 1.08 | 6.5 |
| Between-Day | | | | |
| Control 1 | 10 | 3.86 | 0.93 | 24.0 |
| Control 2 | 10 | 6.60 | 0.77 | 11.7 |
| Control 3 | 10 | 7.60 | 0.55 | 7.2 |
| Control 4 | 10 | 12.05 | 0.79 | 6.6 |
| Control 5 | 10 | 17.86 | 1.70 | 9.7 |

As expected, the precision is best for the control value in the mid-range of the standard curve, where the therapeutic concentration is monitoring, i.e., 10–20 μg/ml.

What is claimed is:

1. A method for determining the concentration of a physiologically active hapten in a concentration range of interest in a sample in which the hapten is soluble which comprises the steps of:
   a. forming a mixture by mixing said sample with a soluble conjugate of said hapten covalently bound to an immunogenic carrier material and an antibody which will selectively bind said conjugate and measuring the optical density of resulting mixture at a wavelength of from 280 to 600 nm,
   b. determining the amount of hapten present by comparing the measured optical density with a standard curve obtained by separately mixing known amounts of said hapten with fixed amounts of said conjugate and said antibody at dilutions of maximum absorbance, determining the optical density of each resulting mixture at a wavelength of from 280 to 600 nm, and plotting decreasing optical density against increasing concentration of hapten, the hapten to immunogenic carrier ratio in said conjugate being such that in the concentration range of interest the average slope of the standard curve is such as to give optimum sensitivity.

2. A method as in claim 1 wherein the conjugate is gentamicin covalently bound to human serum albumin in a gentamicin to albumin ratio of from 17:1 to 24:1.

3. A method as in claim 1 wherein the conjugate is phenytoin covalently bound to human serum albumin in a phenytoin to albumin ratio of from 12:1 to 40:1.

4. A method as in claim 1 wherein the conjugate is phenobarbitol covalently bound to human serum albumin in a phenobarbitol to albumin ratio of from 15:1 to 30:1.

5. A method as in claim 1 wherein the conjugate is theophylline covalently bound to human serum albumin in a theophylline to albumin ratio of from 10:1 to 20:1.

6. A method as in claim 1 wherein the conjugate is tobramycin covalently bound to human serum albumin in a tobramycin to albumin ratio of from 20:1 to 28:1.

7. A method of measuring the amount of free hapten in a sample and involving a competitive immunoprecipitation assay, said method comprising the steps of forming a solution that includes said free hapten and a hapten-carrier conjugate and antibody which will bind with said free hapten and with said conjugate, in which the turbidity of said solution varies to a measurable degree dependent upon the amount of free hapten and the ratio of hapten to carrier in said conjugate in said solution, and determining said solution turbidity by analysis of radiation at a wavelength within the range 280–600 nm directly transmitted through said solution.

8. A method as in claim 7 wherein the conjugate is gentamicin covalently bound to human serum albumin in a gentamicin to albumin ratio of from 17:1 to 24:1.

9. A method as in claim 7 wherein the conjugate is phenytoin covalently bound to human serum albumin in a phenytoin to albumin ratio of from 12:1 to 40:1.

10. A method as in claim 7 wherein the conjugate is phenobarbitol covalently bound to human serum albumin in a phenobarbitol to albumin ratio of from 15:1 to 30:1.

11. A method as in claim 7 wherein the conjugate is theophylline covalently bound to human serum albumin in a theophylline to albumin ratio of from 10:1 to 20:1.

12. A method as in claim 7 wherein the conjugate is tobramycin covalently bound to human serum albumin in a tobramycin to albumin ratio of from 20:1 to 28:1.

* * * * *